United States Patent [19]

Baumgart

[11] Patent Number: 4,966,587
[45] Date of Patent: Oct. 30, 1990

[54] MEDICAL INTROMISSION KIT

[76] Inventor: Rainer Baumgart, Athener Platz 11, 8000 Munich 90, Fed. Rep. of Germany

[21] Appl. No.: 343,271

[22] Filed: Apr. 26, 1989

[30] Foreign Application Priority Data

Apr. 29, 1988 [DE] Fed. Rep. of Germany ....... 3814618

[51] Int. Cl.⁵ ............................................. A61M 5/32
[52] U.S. Cl. .................... 604/164; 604/167; 604/264
[58] Field of Search ............... 604/164, 165, 166, 167, 604/264, 104, 169, 170

[56] References Cited

U.S. PATENT DOCUMENTS

| 3,030,953 | 4/1962 | Koehn | 604/166 |
| 3,500,828 | 3/1970 | Podhora | |
| 4,250,881 | 2/1981 | Smith | 604/166 |
| 4,430,081 | 2/1984 | Timmermans | |

FOREIGN PATENT DOCUMENTS

| 7928830 | 3/1980 | Fed. Rep. of Germany . |
| 3147609 | 6/1983 | Fed. Rep. of Germany . |
| 3229466 | 2/1984 | Fed. Rep. of Germany . |

Primary Examiner—John D. Yasko
Assistant Examiner—Anthony M. Gutowski
Attorney, Agent, or Firm—Wegner & Bretschneider

[57] ABSTRACT

The medical intromission kit comprises an inner sleeve (10), a distal end portion (13) of which tapers externally in the distal direction, the outer sleeve (30), a sleeve (20) intermediate the inner and outer sleeves (10, 30), a seal means (34) at a proximal end portion of the outer sleeve (30) to receive therethrough at least the inner sleeve (10) so as to occlude completely the inner lumen of the outer sleeve (30), and a proximal outer shoulder (15) having an outside diameter not larger than the outside diameter of the intermediate sleeve (20), provided on the distal end portion (13) of the inner sleeve (10), the three sleeves (10, 20, 30) being formed of flexible material and being arranged coaxially for relative axial displacement one within the other between a retracted position wherein the intermediate sleeve (20) is withdrawn into the outer sleeve (30) with the distal end portion (33) of the outer sleeve (30) abutting the proximal outer shoulder (15) of the inner sleeve (10) and being no larger in diameter than the shoulder (15), and an extended position wherein the distal end portion (22) of the intermediate sleeve (20) extends at least to the distal end of the outer sleeve (30) which is enlarged elastically thereby.

6 Claims, 3 Drawing Sheets

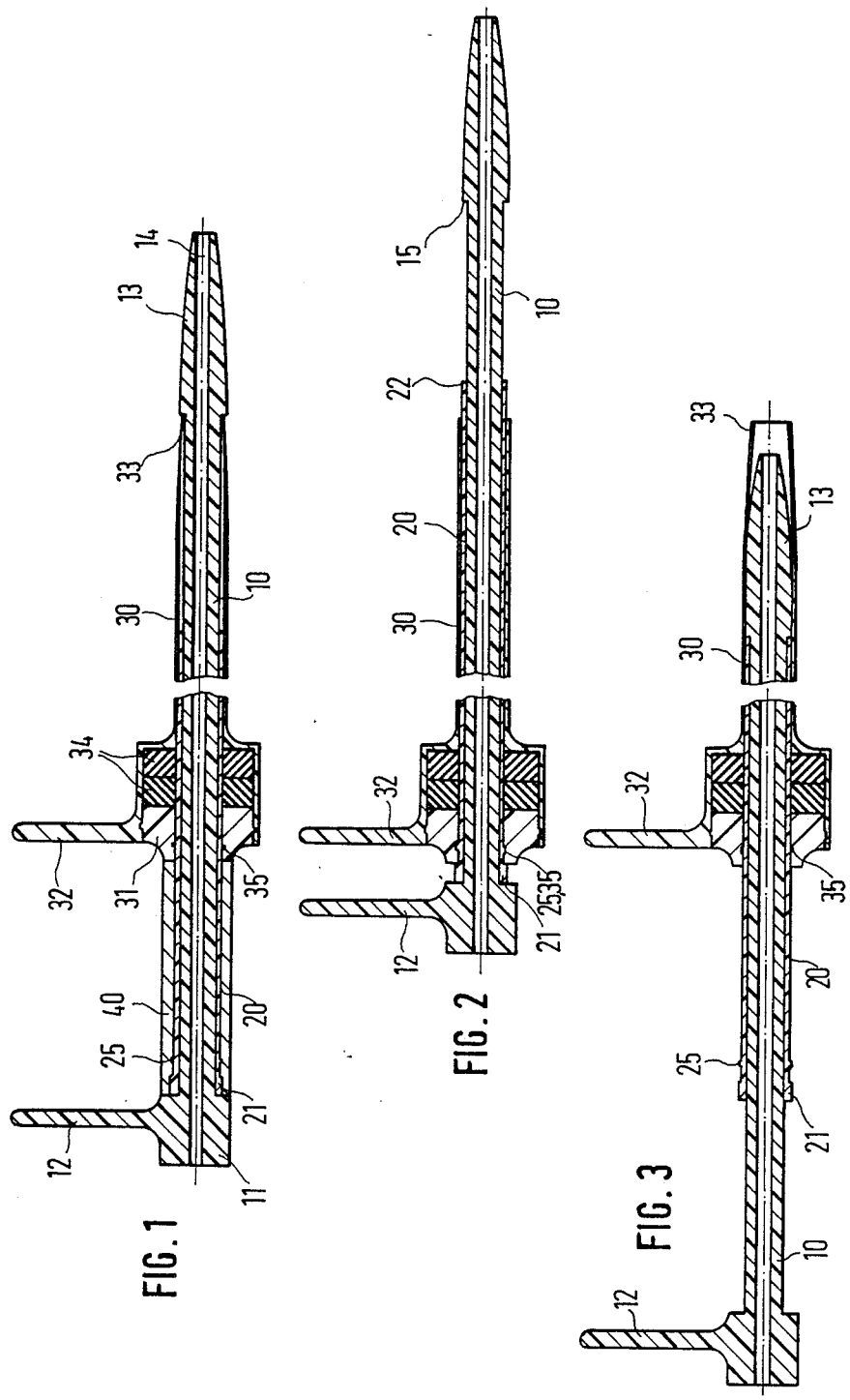

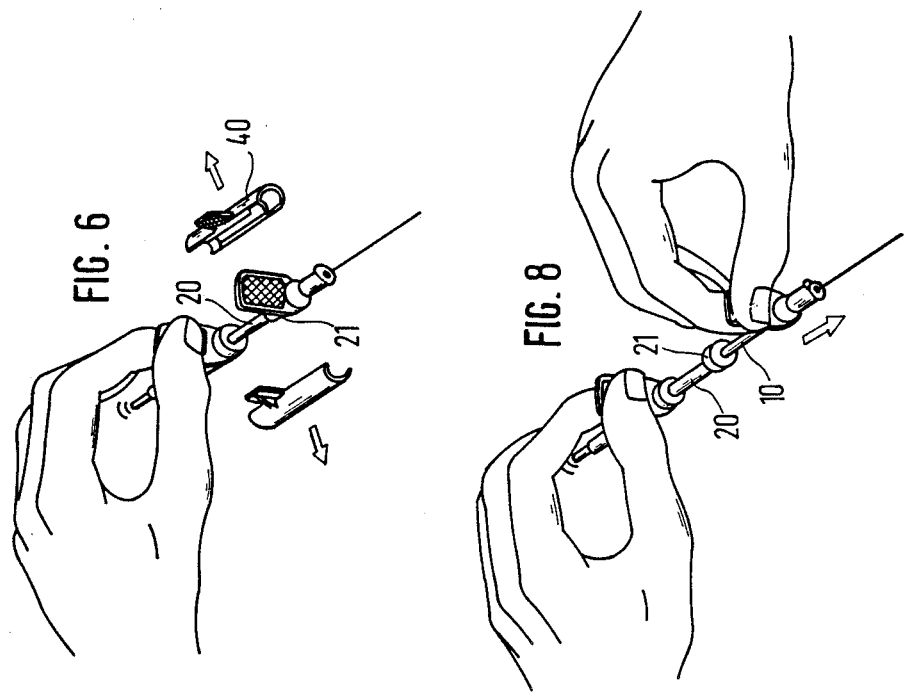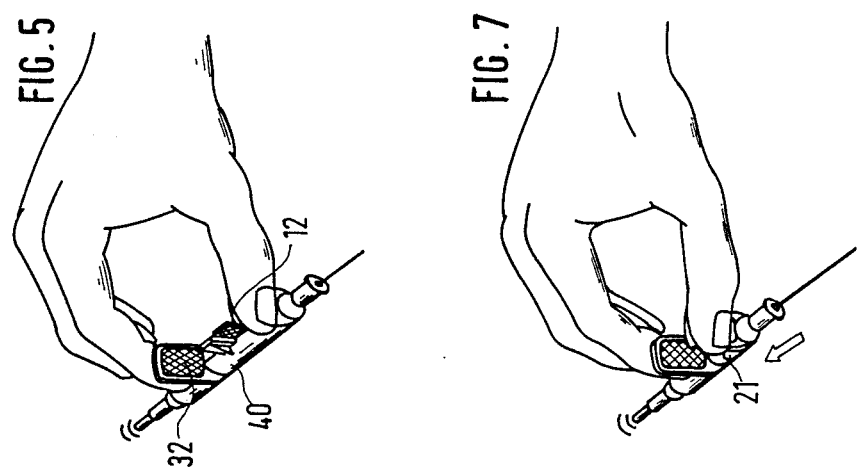

MEDICAL INTROMISSION KIT

BACKGROUND OF THE INVENTION

The invention relates to a medical intromission kit comprising an inner sleeve of flexible material, of which the distal end portion tapers slightly conically in the distal direction while its inside diameter remains the same, and coaxial therewith an outer sleeve of flexible material, of which the proximal end portion includes a seal which allows passage of at least the inner sleeve and occluding completely the inner lumen of the outer sleeve when the inner sleeve is withdrawn, the inner sleeve and the outer sleeve being adapted for axial displacement in respect of each other.

Such an intromission kit is described in U.S. Pat. No. 4,430,081. In most cases, placing of the intromission kit is effected by the so-called Seldinger technique, in which initially for example the artery is punctured with a metal cannula through which a flexible guide wire is pushed into the vascular lumen. Afterwards, the metal cannula is withdrawn. The intromission kit consisting of an inner sleeve and enclosing this an outer sleeve, is then pushed onto the guide wire. At this stage, firstly the end portion of the inner sleeve which tapers conically towards the distal end is introduced into the vascular lumen through the aperture formed by the metal cannula and is pushed sufficiently far forwards, widening out this aperture, for the outer sleeve to be disposed sufficiently far into the vessel.

The inner lumen of the outer sleeve is at the proximal end portion sealed by a packing constituted, for example, by a stellate or round rubber lip, these being disposed one behind the other and fitting closely around the inner sleeve so that no blood can emerge from the artery even when the inner sleeve and the guide wire are withdrawn from the outer sleeve.

The outer sleeve with the proximal seal is also referred to as a plastic sluice. A properly placed sluice can make it possible to pass through quickly and without problem various catheters, endoscopes or other instruments such as, for example, biopsy forceps, without the puncture site being damaged every time there is a change.

Pushed onto the inner sleeve, the outer sleeve forms an annular outer shoulder in relation to the outside diameter of the inner sleeve and by reason of the thin wall thickness of the outer sleeve, upon passage through the vascular opening, causes a slipping-on and piercing of the distal end portion of the outer sleeve and consequently vascular wall lesions or extensive damage to the tissue along the puncture channel in the case of a puncture into parenchymatous organs, unless this damage is recognised at once. It is by no means rare for such damage to cause the emergence of blood if the sluice is recumbent or to secondary bleeding and in isolated cases, in the case of vascular punctures, it may even produce scar-like structures if the vascular lumen becomes torn.

The size of the outside diameter of the outer sleeve is limited by the fact that upon removal of the sluice, closure of the percutaneous puncture aperture should close without any operative procedure, for example in the case of an artery, by compression of approx. 30 to 60 minutes. With increasing outside diameter, furthermore, the wall thickness of the outer sleeve increases, i.e. the step in the intromission direction and thus the above-described risk will be entailed.

SUMMARY OF THE INVENTION

It is the object of the invention to improve the intromission kit of the type referred to above, so that, if an outer sleeve which is as thin-walled as possible, and which has a large inner lumen is used, it is of stepless construction in the intromission direction and so that the sleeves disposed in the outer sleeve can be removed without problem.

According to the invention, this object is achieved with an intromission kit of the type described above by the fact that the distal end portion of the inner sleeve has a proximal outer shoulder, in that between the outer sleeve and the inner sleeve there is a coaxial intermediate sleeve of flexible material adapted for displacement in relation to the inner sleeve and the outer sleeve between a position in which it is drawn into the outer sleeve and a position in which it is pushed out, in that in the drawn-in position of the intermediate sleeve, on the one hand the end face of the distal end portion of the outer sleeve bears on the proximal outer shoulder of the inner sleeve while on the other hand the outside diameter of the end face of the distal end portion of the outer sleeve is of exactly the same size as or is smaller than the outside diameter of the proximal outer shoulder of the inner sleeve, in that in the pushed-out position of the intermediate sleeve the end face of its distal end portion is substantially flush in its alignment with or is distally projecting from the end face of the distal end portion of the outer sleeve which is widened out somewhat elastically by the intermediate sleeve, and in that the outside diameter of the outer shoulder of the inner sleeve is of exactly the same size as or is smaller than the outside diameter of the intermediate sleeve.

If the intromission kit which is so constructed is pushed onto the guide wire which is inserted, for example, into a vascular lumen, and is pushed forwards through the opening and into the vascular lumen, then there will be no step on the outside of the intromission kit in the direction of insertion, since the end face of the outer sleeve, in the direction of insertion, is covered by the proximal outer shoulder of the distal end portion of the inner sleeve. The opening in the vascular wall is thus widened out steplessly upon introduction of the kit, so excluding any possibility of either damage to the distal end portions of the outer sleeve or to the vascular wall.

When the intromission kit has been placed, the inner sleeve and the intermediate sleeve must, jointly with the guide wire, be removed from the sluice formed by the outer sleeve and the proximal seal, in order to leave the working passage clear for catheter use. For this purpose, firstly the inner sleeve and the intermediate sleeve are pushed into the vessel by the same amount, so that the distal end portion of the intermediate sleeve is pushed out of the distal end portion of the outer sleeve, so elastically widening out the outer sleeve so that the inside diameter corresponds to the outside diameter of the intermediate sleeve. The distal end portion of the inner sleeve is now, by pulling on the proximal end, retracted from the outside until it is flush against the distal end face of the intermediate sleeve and can then, upon further pulling towards the proximal end, pass through the widenedout distal end of the outer sleeve. The inner sleeve can then be removed jointly with the intermediate sleeve. The seal at the proximal end of the outer sleeve prevents the emergence of blood or fluid and makes it possible to change a catheter without problem. When the manipulations are completed, the sluice can be simply pulled and the puncture aperture be kept closed by corresponding compression for a predetermined period, until the aperture has closed by itself without any operative measures.

Preferably the intermediate sleeve has at its distal end portion on its inside, a recess which extends axially over the entire inner periphery, and which ends at an inner shoulder, and the outside diameter of the proximal outer shoulder of the inner sleeve is of the same size as or is smaller than the inside diameter of the recess. With such a development, the distal end portion of the inner sleeve can be sufficiently accomodated in the distal recess in the intermediate sleeve until its outer shoulder bears on the inner shoulder of the intermediate sleeve.

If a first handle is mounted on the proximal end portion of the inner sleeve and if a second handle is mounted on the proximal end portion of the outer sleeve, the necessary displacement movements can easily be effected.

Additionally, a removable spacer sleeve can be provided bearing at one end on the proximal end portion of the inner sleeve and on the proximal end portion of the intermediate sleeve and at the other end on the proximal end portion of the outer sleeve. With such an embodiment upon insertion of the intromission kit it is guaranteed that the distal end face of the outer sleeve bears flush on the proximal outer shoulder of the distal end of the inner sleeve and is therefore masked. The spacer sleeve is removed by being folded open when the inner sleeve and intermediate sleeve are required to be withdrawn from the outer sleeve of the placed intromission kit in the manner described hereinabove.

It is convenient to provide an annular groove in the proximal end portion of the outer sleeve and, projecting from the outer surface of the intermediate sleeve, to provide an elastically deformable annular bead wich engages the annular groove in the pushed out position of the intermediate sleeve.

Thereby it is ensured that when the inner sleeve and the intermediate sleeve have to be withdrawn from the outer sleeve, the inner sleeve bears flush on the distal end portion of the intermediate sleeve. Thus, upon withdrawal of the inner sleeve, the intermediate sleeve is initially maintained in the outer sleeve until the proximal outer shoulder of the distal end portion of the inner sleeve presses outside the outer sleeve rigidly against the abutment on the distal end of the intermediate sleeve, so releasing the annular bead on the intermediate sleeve, from the annular groove in the outer sleeve. This ensures that the proximal outer shoulder of the inner sleeve can pass reliably through the distal aperture of the outer sleeve, so that the inner sleeve and the intermediate sleeve can be removed without problem. With this arrangement, furthermore, when the annular bead is clear of the annular groove, the intermediate sleeve directly follows the movement of the inner sleeve and requires no additional grip.

The described intromission kit is used for punctures into vessels, bodily cavities, organs in bodily cavities and parenchymatous organs such as, for example, in the case of arterial, venous, bladder, pleural, cystic duct, uteral, peritoneal or liver punctures.

Further favourable embodiments of the invention result from the following description.

BRIEF DESCRIPTION OF THE DRAWINGS

FIG. 1 is a cross-section through the intromission kit in the insertion situation;

FIG. 2 is a view similar to FIG. 1 showing the intromission kit in an initial stage for withdrawal of the inner sleeve and intermediate sleeve from the sluice;

FIG. 3 shows in a view as in FIG. 1 the intromission kit in a situation in which the inner sleeve and the intermediate sleeve can be withdrawn from the sluice;

FIG. 5 shows in a perspective view the operation of the intromission kit upon insertion over the recumbent guide wire;

FIG. 6 is a perspective view showing the opening-up of the spacer sleeve;

FIG. 7 is a perspective view showing the procedure when displacing the inner sleeve and entraining the intermediate sleeve, and FIG. 8 is a perspective view showing the procedure when withdrawing the inner sleeve and entraining the intermediate sleeve.

DETAILED DESCRIPTION OF THE INVENTION

Figure 4:
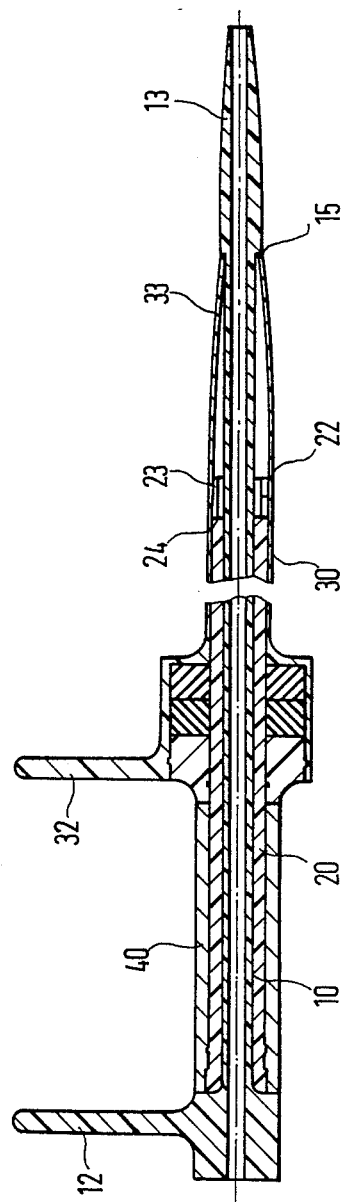
FIG. 4 shows in cross-section a modified embodiment of the distal end portion of the intermediate sleeve.

The intromission kit shown in the drawings consists of three tubular sleeves of flexible material, namely an outer sleeve 30, an intermediate sleeve 20, and an inner sleeve 10 which are pushed coaxially one onto another, being adapted for displacement relatively to one another at specific axial distances.

The inner sleeve 10 has at its proximal end portion 11 a handle 12. The distal end portion 13 of the inner sleeve 10 has the same inner lumen 14 as the other end of the inner sleeve 10 but its wall thickness is greater than that of the proximal end of the other inner sleeve 10 so that proximally an outer shoulder 15 is formed from which the distal end portion 13 narrows towards the intromission end.

The intermediate sleeve 20 has a proximal cylindrical end portion 21, of which the outside diameter is greater than the outside diameter of the intermediate sleeve 20. This outside diameter of the intermediate sleeve 20 is at least as great as the outside diameter of the proximal outer shoulder 15 of the distal end portion 13 of the inner sleeve 10.

In the case of the modified embodiment shown in FIG. 4, there is in the distal end portion 22 of the intermediate sleeve 20 a recess 23 starting from the end face and extending over the entire peripheral surface, ending at an inner shoulder 24. The inside diameter of the recess 23 is equal to or larger than the outside diameter of the distal end portion 13 of the inner sleeve 10 in the region of the outer shoulder 15 on the inner sleeve 10 so that the distal end portion 13 on the side of the proximal outer shoulder 15 can be pushed onto the recess 23.

The outer sleeve 30 has a proximal portion 31 with a handle 32 and accomodates two seals 34 of which one is stellate while the other is annular in construction and in most cases they are made from rubber which is thus elastically deformable so that the intermediate sleeve 20 with the inner sleeve 10 can be pushed through the seals 34 and so that these seals 34 completely occlude the inner lumen of the outer sleeve 30 when the intermediate sleeve 20, together with the inner sleeve 10, is withdrawn from the outer sleeve 30 in order, for example, to be able to insert a catheter. Starting from its proximal portion 31, the outer sleeve 30 is of thin-walled construction and has a slightly conically tapering but radially elastically openable end portion 33, which has at its distal end an outside diameter which is equal to or slightly smaller than the outside diameter of the distal end portion 13 of the inner sleeve 10 in the region of the proximal outer shoulder 15.

As FIG. 1 shows, the end face of the distal end portion 33 of the outer sleeve 30 bears on the proximal outer shoulder 15 of the thickened distal end portion 13 of the inner sleeve 10, the proximal end portion 11 of the inner sleeve 10, the proximal end portion 21 of the intermediate sleeve 20, and the proximal end portion 31 of the outer sleeve 30 being fixed by an openable spacer sleeve 40, as shown in FIG. 5. In this arrangement, the intromission kit has an outside diameter which increases gradually and steplessly from its distal end in the direction of its proximal end, allowing the intromission kit to be introduced into a vascular aperture without the thin-walled outer sleeve 30 folding over or tearing at the distal end.

Cut into the proximal end portion 31 of the outer sleeve 30 is an annular groove 35. Projecting from the outer surface of the intermediate sleeve 20 is an annular bead 25 which is elastically deformable and which, in the fully distally pushed-out position of the intermediate sleeve 20, engages the annular groove 35 as shown in FIG. 2.

If, then, the inner sleeve 10 and the intermediate sleeve 20 have to be removed from the sluice, in other words from the outer sleeve 30 with the seals 34, the spacer sleeve 40 is removed by opening up, as shown in FIG. 6. The proximal end portion 11 of the inner sleeve 10 is, by means of the handle 12 and together with the adjacent proximal end portion 21 of the intermediate sleeve 20, displaced towards the proximal end portion 31 of the outer sleeve 30 until the proximal end portions 11, 21 of the inner sleeve 10 and intermediate sleeve 20 respectively bear on the proximal end portion 31 of the outer sleeve 30, as shown in FIGS. 2 and 7. At the end of this displacement the annular bead 25 of the intermediate sleeve 20 engages the annular groove 35 in the proximal end portion 31 of the outer sleeve 30. Furthermore, during this displacement, the distal end portion 22 of the intermediate sleeve 20 widens out the distal end portion 33 of the outer sleeve 30, so that the outside diameter of the intermediate sleeve 20 corresponds to the inside diameter of the outer sleeve 30 at its distal end portion 33. As can be seen from FIG. 2, the intermediate sleeve 20 projects beyond the distal end face of the outer sleeve 30.

By pulling away the handle 12 on the inner sleeve 10 from the handle 32 on the outer sleeve 30 in a proximal direction, firstly the thickened distal end portion 13 of the inner sleeve 10 is pulled with its proximal outer shoulder 15 flush against the distal end face of the intermediate sleeve 20. In the modified embodiment shown in FIG. 4, the distal end portion 13 of the inner sleeve 10 is pulled into the recess 23 in the intermediate sleeve 20 until the outer shoulder 15 on the inner sleeve 10 bears on the inner shoulder 24 on the intermediate sleeve 20.

By further pulling on the handle 12 on the inner sleeve 10, and after a slight resistance has been overcome, the annular bead 25 on the intermediate sleeve 20 becomes disengaged from the annular groove 35 on the proximal end portion 31 of the outer sleeve 30. While retaining contact between its distal end portion 22 and the proximal outer shoulder 15, the intermediate sleeve 20 follows the retraction movement of the inner sleeve 10, as FIG. 8 shows, and slides into the distal end portion 33 of the outer sleeve 30, as shown in FIG. 3. From this position, the inner sleeve 10 and the intermediate sleeve 20 can without difficulty be withdrawn from the sluice constituted by the outer sleeve 30 and the seals 34, in a proximal direction.

What is claimed is:

1. A medical intromission device comprising:
   an inner sleeve having a slightly conical, tapering distal end portion, wherein the distal end portion includes a shoulder having an outer diameter and said shoulder extends proximally from the distal end portion,
   an intermediate sleeve coaxial with the inner sleeve, wherein the intermediate sleeve has a distal end for engaging with the shoulder of the distal end portion of the inner sleeve, said distal end of the intermediate sleeve having an outer diameter greater than or equal to the outer diameter of the shoulder of the distal end portion,
   a flexible outer sleeve coaxial with the intermediate sleeve, said outer sleeve having a distal end with an outer diameter less than or equal to the outer diameter of the shoulder of the distal end portion of the inner sleeve and having a proximal end with a seal for occluding flow through the outer sleeve when the inner sleeve and intermediate sleeve are removed from the outer sleeve, and
   wherein the inner and intermediate sleeves are removable from the outer sleeve by pushing the intermediate sleeve through the outer sleeve to widen the distal end of the outer sleeve and retracting the inner sleeve to engage the shoulder of the distal end portion with the intermediate sleeve before passing through the distal end of the outer sleeve and out through the seal of the proximal end of the outer sleeve.

2. A medical intromission device of claim 1, comprising a recess and inner shoulder at the distal end of the intermediate sleeve.

3. A medical intromission device of claim 2, comprising a handle at a proximal end portion of the inner sleeve and a handle at the proximal end of the outer sleeve.

4. A medical intromission device of claim 1, comprising a handle at a proximal end portion of the inner sleeve and a handle at the proximal end of the outer sleeve.

5. A medical intromission device of claim 1, comprising a removable spacer sleeve bearing at a proximal end of the inner sleeve and at a proximal end of the intermediate sleeve.

6. A medical intromission device of claim 1, comprising an annular groove at the proximal end of the outer sleeve and an elastically deformable annular bead at a proximal end portion of the intermediate sleeve for engaging the annular groove.

* * * * *